United States Patent
Maruyama

(10) Patent No.: US 11,141,381 B2
(45) Date of Patent: Oct. 12, 2021

(54) COMPOSITION FOR ENTERIC HARD CAPSULE AND METHOD FOR PRODUCING ENTERIC HARD CAPSULE

(71) Applicant: SHIN-ETSU CHEMICAL CO., LTD., Tokyo (JP)

(72) Inventor: Naosuke Maruyama, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/641,952

(22) Filed: Jul. 5, 2017

(65) Prior Publication Data

US 2018/0015045 A1 Jan. 18, 2018

(30) Foreign Application Priority Data

Jul. 12, 2016 (JP) .............................. JP2016-137616

(51) Int. Cl.
| | |
|---|---|
| *A61K 9/48* | (2006.01) |
| *A61K 47/38* | (2006.01) |
| *B29C 41/14* | (2006.01) |
| *B29K 1/00* | (2006.01) |

(52) U.S. Cl.
CPC ............ *A61K 9/4816* (2013.01); *A61K 47/38* (2013.01); *B29C 41/14* (2013.01); *B29K 2001/12* (2013.01)

(58) Field of Classification Search
None
See application file for complete search history.

(56) References Cited

U.S. PATENT DOCUMENTS

| | | | | |
|---|---|---|---|---|
| 4,365,060 | A | * 12/1982 | Onda ................... | A61K 9/4816 424/451 |
| 9,890,221 | B2 | * 2/2018 | Yin ......................... | C08B 13/00 |
| 2012/0161364 | A1 | 6/2012 | Son et al. | |

FOREIGN PATENT DOCUMENTS

| | | | |
|---|---|---|---|
| EP | 2 476 439 | A1 | 7/2012 |
| EP | 2837391 | * | 2/2015 |
| JP | S58-138458 | A | 8/1983 |
| JP | 2006-016372 | A | 1/2006 |
| JP | 2013-504565 | A | 2/2013 |
| JP | 2015-518005 | A | 6/2015 |
| JP | 2015-529727 | A | 10/2015 |
| WO | 2013/164121 | A1 | 11/2013 |
| WO | 2014/031419 | A1 | 2/2014 |
| WO | 2015/179072 | A1 | 11/2015 |

OTHER PUBLICATIONS

PubChem, D-Glucose, https://pubchem.ncbi.nlm.nih.gov/compound/D-glucose, obtained online on Apr. 24, 2018 (Year: 2018).*
Nov. 10, 2017 Extended European Search Report issued in European Patent Application No. EP 17180870.2.
Jan. 22, 2019 Office Action issued in Japanese Application No. 2006-137616.

* cited by examiner

*Primary Examiner* — Jennifer A Berrios

(74) *Attorney, Agent, or Firm* — Oliff PLC

(57) ABSTRACT

A composition for an enteric hard capsule by taking advantage of conventionally unknown thermal gelation characteristics of a neutralized aqueous solution of an enteric polymer, so as to obtain an enteric capsule having sufficient water and acid resistances. More specifically, the composition has hypromellose acetate succinate having a molar substitution with an acetyl group per anhydroglucose unit of 0.6 to 0.8 and a ratio of the molar substitution with an acetyl group to a molar substitution with a succinyl group per anhydroglucose unit of 2.0 to 4.0, a neutralizer, and water method produces an enteric hard capsule having the steps of: immersing a core pin heated at 50 to 80° C. in the composition, taking the immersed core pin out of the composition, and drying a gel layer of the hypromellose acetate succinate formed on the taken-out core pin.

20 Claims, No Drawings

COMPOSITION FOR ENTERIC HARD CAPSULE AND METHOD FOR PRODUCING ENTERIC HARD CAPSULE

BACKGROUND OF THE INVENTION

1. Field of the Invention

The present invention relates to a composition for an enteric hard capsule and a method for producing an enteric hard capsule. More specifically, the present invention relates to a composition for an enteric hard capsule, the composition comprising hypromellose acetate succinate (another name: hydroxypropyl methyl cellulose acetate succinate, hereinafter also called "HPMCAS"), a neutralizer, and water; and a method for producing an enteric hard capsule.

2. Description of the Related Art

The dosage form used for pharmaceutical products, health foods and the like includes a capsule, a tablet and a granule. The capsule is useful because an active component can be easily encapsulated.

The capsule includes a soft capsule and a hard capsule, and the hard capsule includes a gelatin capsule made from gelatin and a cellulose capsule made from hypromellose (another name: hydroxypropyl methyl cellulose, hereinafter also called "HPMC").

As compared with the gelatin, the HPMC has no possibility of mad cow disease, is derived from a plant, and provides high capsule strength even at low water content of the capsule. Hence, the HPMC has been widely used as a base material of the cellulose capsule.

The method for producing a cellulose capsule is typically exemplified by a cool gelation method using a gelling agent and a thermal gelation method. In each method, a core pin is immersed in a certain aqueous HPMC solution or a certain HPMC slurry, and then is taken out of the immersion bath to allow the HPMC to gelate. This prevents dripping and allows the HPMC liquid to uniformly adhere onto the core pin. After subsequent drying, a hard capsule with a uniform film thickness can be produced. Thus, the gelation is an important characteristic in the production of uniform capsule.

In the cool gelation method, a substance that gelates at normal temperature is used as the gelling agent. Examples of the gelling agent include carrageenan, gellan gum, pectin, agar, and sodium alginate. A core pin is immersed in a hot water slurry containing HPMC and a gelling agent to allow a predetermined amount of the hot water slurry to adhere onto the core pin, and then the slurry on the pin is cooled to gelate.

In the thermal gelation method, such characteristics that an aqueous HPMC solution gelates thermally is utilized. In the method, a heated core pin is immersed in an aqueous HPMC solution, and the aqueous HPMC solution gelates on and adheres to the heated core pin.

However, both the gelatin capsule and the cellulose capsule are water-soluble and thus disintegrate in gastric juice after oral administration. When the capsule contents such as a pharmaceutical product or a health food are unstable in an acid or irritate the stomach, such a capsule is unsuitable for use. In such a case, a hard capsule is coated with an enteric polymer. This method, however, needs an additional coating step, resulting in poor productivity and high cost. To address this problem, a hard capsule has been developed by using an enteric polymer itself as a capsule base material.

There has been provided an enteric hard capsule comprising an enteric cellulose derivative such as hypromellose phthalate (another name: hydroxypropyl methyl cellulose phthalate, hereinafter also called "HPMCP") or HPMCAS; a nonpolar gelling agent; and at least one plasticizer selected from triethyl citrate, triacetin, glycerol fatty acid esters, polysorbate 80 (Tween 80) and polyethylene glycol (JP 2006-016372A).

There is also provided an aqueous composition for an enteric hard capsule, the composition comprising at least one substance selected from the group consisting of HPMCP and HPMCAS as the enteric base material; at least one cellulose ether selected from the group consisting of hydroxypropyl methyl cellulose (HPMC) and methyl cellulose (MC) as a capsule molding aid; and an alkaline neutralizer (JP 2013-504565T, which is a Japanese phase publication of WO 2011/030952).

There is provided an aqueous composition for producing an enteric hard capsule shell, the composition comprising an aqueous dispersion of HPMCAS partially neutralized with at least one alkaline substance (JP 2015-518005T, which is a Japanese phase publication of WO 2013/164,121).

SUMMARY OF THE INVENTION

However, in the production of the enteric hard capsule disclosed in JP 2006-016372A, a water-soluble gelling agent or plasticizer is required in a large amount, so that the resulting capsule disintegrates in water and exhibits insufficient acid resistance in an acidic test liquid.

In the production of an enteric hard capsule from the aqueous composition disclosed in JP 2013-504565T, a large amount of a water-soluble cellulose ether is required as the gelling agent, so that the resulting capsule disintegrates in water and exhibits insufficient acid resistance in an acidic test liquid.

The enteric hard capsule shell disclosed in JP 2015-518005T is produced from an aqueous dispersion of an enteric polymer, so that it is difficult to form a uniform film. In the production of the enteric hard capsule shell, a water-soluble gelling agent or plasticizer is required in a large amount, so that the resulting capsule disintegrates in water and exhibits insufficient acid resistance in an acidic test liquid.

As described above, each conventional method requires a water-soluble gelling agent so that there is a problem that the resulting enteric capsule exhibits insufficient water resistance or acid resistance.

An object of the present invention is to provide a composition for an enteric hard capsule and a method for producing an enteric hard capsule by taking advantage of conventionally unknown thermal gelation characteristics of a neutralized aqueous solution of an enteric polymer, so as to produce an enteric capsule having sufficient water resistance and acid resistance, As a result of intensive studies for achieving the above object, the inventors have found that certain HPMCAS has excellent thermal gelation characteristics, and have completed the invention. The inventors have further found that by using a composition for an enteric hard capsule, the composition comprising the HPMCAS, a neutralizer and water, the enteric hard capsule having excellent water resistance, acid resistance and mechanical strength can be produced.

In an aspect of the invention, there can be provided a composition for an enteric hard capsule, the composition comprising hypromellose acetate succinate having a molar substitution with an acetyl group per anhydroglucose unit of 0.6 to 0.8 and a ratio of the molar substitution with an acetyl group to a molar substitution with a succinyl group per anhydroglucose unit of 2.0 to 4.0; a neutralizer; and water.

In another aspect of the invention, there can provided a method for producing an enteric hard capsule, comprising the steps of: immersing a core pin heated at 30 to 80° C. in the composition for an enteric hard capsule comprising the hypromellose acetate succinate; taking the immersed core pin out of the composition; and drying a gel layer of the hypromellose acetate succinate formed on the taken-out core pin.

According to the invention, a high quality enteric hard capsule having excellent water resistance, acid resistance and mechanical strength and having an enhanced appearance can be produced. The HPMCAS is a plant-derived cellulose derivative so that it is free from the contamination with mad cow disease and the capsule comprising the HPMCAS can be provided stably in the market. In addition, conventional facilities can be used without modification so that industrial mass-production of the capsule is made possible.

DETAILED DESCRIPTION OF THE PREFERRED EMBODIMENTS

The composition for an enteric hard capsule is preferably an aqueous composition comprising HPMCAS having a particular substitution degree, a neutralizer, and water, wherein the aqueous composition is an aqueous solution in which water-insoluble acidic polymer HPMCAS is dissolved by neutralization with a neutralizer.

The HPMCAS having a particular substitution degree is used as the base material for an enteric hard capsule. The base material for the enteric hard capsule is typically and preferably a cellulose derivative such as hypromellose phthalate (HPMCP) and HPMCAS, which provides a film having excellent mechanical characteristics, transparency, gas barrier properties and the like. According to the invention, HPMCAS having a particular substitution degree is selected.

The HPMCAS is a cellulose derivative having four types of substituents: a hydroxypropoxy group, a methoxy group, an acetyl group and a succinyl group, on cellulose. The substitution degrees of the four types of substituents of HPMCAS can be determined by the method described in "hypromellose acetate succinate" in Official Monographs in the Japanese Pharmacopoeia Seventeenth Edition, Supplement I.

The HPMCAS has a molar substitution with an acetyl group per anhydroglucose unit of 0.6 to 0.8, preferably 0.60 to 0.75, more preferably 0.60 to 0.70. HPMCAS having a molar substitution with an acetyl group of less than 0.6 exhibits insufficient thermal gel strength. HPMCAS having a molar substitution with an acetyl group of more than 0.8 provides a composition for an enteric hard capsule having a lower flowability at normal temperature.

The HPMCAS has a ratio of the molar substitution with an acetyl group per anhydroglucose unit to the molar substitution with a succinyl group per anhydroglucose unit (acetyl group molar substitution/succinyl group molar substitution) of 2.0 to 4.0, preferably 2.3 to 4.0, more preferably 2.5 to 3.7. HPMCAS having the ratio of less than 2.0 exhibits insufficient gel strength. HPMCAS having the ratio of more than 4.0 provides a composition for an enteric hard capsule having a lower flowability at normal temperature.

The molar substitution with a succinyl group per anhydroglucose unit of the HPMCAS is not particularly limited, and is preferably 0.15 to 0.40, more preferably 0.15 to 0.35, even more preferably 0.15 to 0.30.

The molar substitution with a methoxy group per anhydroglucose unit of the HPMCAS is not particularly limited, and is preferably 1.0 to 2.9, more preferably 1.4 to 2.0, even more preferably 1.7 to 2.0.

The molar substitution with a hydroxypropoxy group per anhydroglucose unit of the HPMCAS is not particularly limited, and is preferably 0.1 to 1.0, more preferably 0.1 to 0.8, and even more preferably 0.15 to 0.28.

The thermal gel characteristics of HPMCAS are evaluated by using the relation between storage modulus G'(5 to 90° C.) and loss modulus G". Generally, the loss modulus G" represents a viscous component of a solution, or a component having such characteristics to generate resistance to fluid deformation by fluid movement.

The storage modulus G'(5 to 90° C.) and the loss modulus G" can be determined with, for example, a rheometer MCR 301 manufactured by Anton Paar.

The storage modulus G' (5 to 90° C.) and the loss modulus G" can be determined by a method comprising the steps of: adjusting a sample measurement section of a rheometer at a temperature of 5° C. in advance; placing in the sample measurement section a sample which is a 15% by weight aqueous HPMCAS solution neutralized with an equivalent amount of ammonia, while keeping 0.5 mm of the measurement gap by using parallel plates having a diameter of 50 mmϕ (PP-50) as the measurement jigs; allowing the sample to stand at 5° C. for 5 minutes, while covering an outer periphery of the measurement jigs with silicone oil; and then starting the measurement by applying a distortion with an amplitude of 1% at a frequency of 1 Hz. The sample measurement section is heated to 90° C. at 2° C./min with a Peltier temperature controller. The data are collected at two points per minute. The storage modulus G'(5 to 90° C.) and the loss modulus G" determined by the measurement are variable as the temperature of a measurement system increases. The temperature at which the storage modulus G' (5 to 90° C.) is equal to the loss modulus G", in other words, the temperature at which the ratio of G"/G' becomes 1, is regarded as the gelation temperature. When a heated core pin is immersed in a composition for an enteric hard capsule, the surface temperature of the core pin is assumed to be around 60° C. Hence, the storage modulus G' at 60° C. is evaluated as the gel strength.

The 15% by weight aqueous HPMCAS solution, which is produced by neutralization with ammonia in an amount equivalent to the molar substitution with a succinyl group, has a gelation temperature of preferably 5 to 60° C., more preferably 10 to 60° C., even more preferably 15 to 50° C. When the gelation temperature is less than 5° C., which is excessively low, such a composition for an enteric hard capsule may have a lower flowability at normal temperature. When the gelation temperature is more than 70° C., such a composition may drip during molding to form a capsule so that the capsule may not have a uniform film thickness.

The 15% by weight aqueous HPMCAS solution neutralized with ammonia in an amount equivalent to the molar substitution with a succinyl group preferably has a gel strength at 60° C. of 10 Pa or more, more preferably 20 Pa or more, even more preferably 40 Pa or more. When the gel strength is less than 10 Pa, such a composition may drip during molding to form a capsule so that the capsule may not have a uniform film thickness. The upper limit of the gel strength is not particularly limited, and is preferably 1,000 Pa or less from the standpoint of film thickness control.

The viscosity at 20° C. of a 2% by weight solution of HPMCAS in dilute (0.1 mol/L) aqueous sodium hydroxide is preferably 2.0 to 20 mPa·s, more preferably 2.4 to 3.6 mPa·s from the standpoint of mechanical strength and capsule molding control. The viscosity can be determined by the method using an Ubbelohde-type viscometer described in Viscosity Determination of General Tests of HPMCAS in the Japanese Pharmacopoeia Seventeenth Edition.

The HPMCAS can be produced, for example, by the method described in JP 54-061282A. HPMC as a starting material is dissolved in glacial acetic acid, then subjected to addition of acetic anhydride and succinic anhydride as esterification agents and sodium acetate as a reaction catalyst, and heated for the reaction. After the completion of the reaction, a large amount of water is added to the reaction solution to allow HPMCAS to precipitate. The precipitate is washed with water and then dried to obtain the target HPMCAS.

The concentration of the HPMCAS in the composition for an enteric hard capsule is preferably 10 to 25% by weight, more preferably 10 to 20% by weight from the standpoint of uniformity of the capsule film thickness.

The neutralizer is exemplified by alkaline substances including ammonia, sodium hydroxide, calcium hydroxide, potassium hydroxide and a mixture thereof. A capsule film containing a smaller amount of a residual alkali exhibits higher water resistance and enteric properties, so that the neutralizer is preferably ammonia, which volatilizes and is unlikely to remain in a capsule film after drying.

The amount of the neutralizer is such an amount as to be required to neutralize the HPMCAS and obtain a transparent aqueous solution, and is preferably 80 to 120% by mole, relative to the molar substitution with a succinyl group (100%) in the HPMCAS.

The water content of the composition for an enteric hard capsule depends on the HPMCAS concentration or the neutralizer content, and is preferably 70 to 90% by weight.

The composition for an enteric hard capsule basically does not require a water-soluble gelling agent, but may contain the water-soluble gelling agent to further improve the strength. Examples of the water-soluble gelling agent include MC, HPMC, carrageenan, gellan gum, pectin, agar, and sodium alginate. The content of the water-soluble gelling agent is preferably 4% by weight or less, more preferably 1% by weight or less, even more preferably 0.5% by weight or less from the standpoint of the water resistance, the acid resistance and the mechanical strength of an enteric capsule.

The composition for an enteric hard capsule can contain an optional plasticizer such as triethyl citrate, triacetin, a glycerol fatty acid ester, polysorbate 80 and polyethylene glycol; and an optional pigment such as titanium oxide and aluminum lake. The content of the plasticizer is preferably 0 to 15% by weight. The content of the pigment is preferably 0 to 10% by weight.

The method for producing the composition for an enteric capsule is not particularly limited, and exemplified by a method in which HPMCAS is dispersed in water and then a neutralizer is added thereto to obtain an aqueous solution. Specific examples include a method in which HPMCAS is added to water, dispersed with a propeller stirrer, a homogenizer or the like to obtain an aqueous HPMCAS dispersion, and subjected to addition of a neutralizer. The rotation rate of the propeller stirrer is 100 to 1,200 rpm, and the rotation rate of the homogenizer is preferably 500 to 10,000 rpm, from the standpoint of maintaining comparatively mild stirring of the dispersion to prevent the polymer from aggregating due to bubbling. The temperature during preparation is preferably 5 to 60° C., more preferably 10 to 30° C. from the standpoint of cooling time or uniformity of the capsule film thickness.

The viscosity at 20° C. of the composition for an enteric hard capsule is not particularly limited, and is preferably 100 to 10,000 mPa·s, more preferably 1,000 to 5,000 mPa·s from the standpoint of the film thickness control of an enteric hard capsule. The viscosity of the composition for an enteric hard capsule can be determined by a type B viscometer, which is a Brookfield type viscometer, described in viscosity measurement in General Tests of the Japanese Pharmacopoeia.

In the immersion step for producing an enteric hard capsule, a core pin heated at 30 to 80° C. is immersed in a hypromellose acetate succinate-containing composition for an enteric hard capsule. Before the immersion, the core pin is heated preferably at 30 to 80° C., more preferably at 50 to 80° C. When a core pin has a temperature of less than 30° C., the gelation may be insufficient when the core pin is immersed in the composition for an enteric hard capsule, and the composition may drip from the core pin. When a core pin has a temperature of more than 80° C., the result or effect is not changed.

The immersion time in the composition for an enteric hard capsule is preferably 1 to 10 seconds, more preferably 2 to 6 seconds from the standpoint of the adhesion amount to the core pin.

In the core pin take-out step for producing an enteric hard capsule, the immersed core pin is taken out of the composition for an enteric hard capsule. The time for taking out the core pin is preferably 1 to 30 seconds, more preferably 5 to 10 seconds from the standpoint of the adhesion amount to the core pin.

In the drying step for producing an enteric hard capsule, the gel layer of the hypromellose acetate succinate formed on the taken-out core pin is dried. The temperature for drying the gel layer formed on the core pin is preferably 40 to 80° C., more preferably 50 to 70° C. from the standpoint of productivity or the surface smoothness of a hard capsule.

The time for drying the gel layer formed on the core pin varies depending on the drying temperature or a type of apparatus, and is preferably 0.5 to 3 hours, more preferably 1 to 2 hours from the standpoint of sufficient drying or productivity.

Examples of the hard capsule size includes size 00, size 0, size 1, size 2, size 3, size 4, size 5 and size 9. In the invention, hard capsules with any size can be produced and used. The produced enteric hard capsule is a high quality enteric hard capsule having excellent water resistance, acid resistance and mechanical strength and having an enhanced appearance, so that it is suitable for pharmaceuticals, health foods, and the like.

The drug or the active ingredient to be encapsulated in the capsule may be any substance that can be orally administered. Examples of the drug include drugs for the central nervous system, drugs for the cardiovascular system, drugs for the respiratory system, drugs for the digestive system, antibiotics, antitussives and expectorants, antihistamines, antipyretic anti-inflammatory analgesics, diuretics, autonomic agents, antimalarial agents, antidiarrheal agents, psychotropics, and vitamins and derivatives thereof.

Examples of the drug for the central nervous system include diazepam, idebenone, aspirin, ibuprofen, paracetamol, naproxen, piroxicam, diclofenac, indomethacin, sulindac, lorazepam, nitrazepam, phenytoin, acetaminophen, ethenzamide, ketoprofen, and chlordiazepoxide.

Examples of the drug for the cardiovascular system include molsidomine, vinpocetine, methyldopa, dipyridamole, furosemide, triamterene, nifedipine, atenolol, spironolactone, metoprolol, pindolol, captopril, isosorbide dinitrate, delapril hydrochloride, meclofenoxate hydrochloride, diltiazem hydrochloride, etilefrine hydrochloride, digitoxin, propranolol hydrochloride, and alprenolol hydrochloride.

Examples of the drug for the respiratory system include amlexanox, dextromethorphan, theophylline, pseudoephedrine, salbutamol, and guaifenesin.

Examples of the drug for the digestive system include benzimidazole drugs having antiulcer action, such as 2-[[3-methyl-4-(2,2,2-trifluoroethoxy)-2-pyridyl]methylsulfinyl] benzimidazole and 5-methoxy-2-[(4-methoxy-3,5-dimethyl-2-pyridyl)methylsulfinyl]benzimidazole; cimetidine; ranitidine; pirenzepine hydrochloride; pancreatin; bisacodyl; and 5-aminosalicylic acid.

Examples of the antibiotic include talampicillin hydrochloride, bacampicillin hydrochloride, cefaclor, and erythromycin.

Examples of the antitussive and expectorant include noscapine hydrochloride, carbetapentane citrate, dextromethorphan hydrobromide, isoaminile citrate, and dimemorfan phosphate.

Examples of the antihistamine include chlorpheniramine maleate, diphenhydramine hydrochloride, and promethazine hydrochloride.

Examples of the antipyretic anti-inflammatory analgesic include ibuprofen, diclofenac sodium, flufenamic acid, sulpyrine, aspirin, and ketoprofen.

Examples of the diuretic include caffeine.

Examples of the autonomic agent include dihydrocodeine phosphate, dl-methylephedrine hydrochloride, atropine sulfate, acetylcholine chloride, and neostigmine.

Examples of the antimalarial agent include quinine hydrochloride.

Examples of the antidiarrheal agent include loperamide hydrochloride.

Examples of the psychotropic include chlorpromazine.

Examples of the vitamins and derivatives thereof include vitamin A, vitamin B1, fursultiamine, vitamin B2, vitamin B6, vitamin B12, vitamin C, vitamin D, vitamin E, vitamin K, calcium pantothenate, and tranexamic acid.

EXAMPLES

The invention will next be described in further detail with reference to Examples and Comparative Examples. It should not be construed that the invention is limited to or by description of Examples.

Example 1

The 15 parts by weight of HPMCAS having substitution degrees shown in Table 1 was added to 83.13 parts by weight of water of 15° C., dispersed with a stirrer, and then subjected to addition of 1.87 parts by weight of 10% by weight aqueous ammonia (molar amount equivalent to that of the succinyl group) to prepare a test liquid for measurement of thermal gel characteristics of the HPMCAS. The thermal gel characteristics of the test liquid were evaluated on basis of the relation between storage modulus G'(5 to 90° C.) and loss modulus G" determined by using a rheometer, MCR 301, manufactured by Anton Paar. The temperature at which the storage modulus G'(5 to 90° C.) is equal to the loss modulus G" is shown as the gelation temperature, and the storage modulus G' at 60° C. is shown as the gel strength in Table 1.

Next, the test liquid was used as a composition for an enteric hard capsule. A cylindrical core pin (size 0) having a diameter of 7 mm and a height of 22 mm and heated at 70° C. was immersed in the composition for an enteric hard capsule adjusted at 15° C. for 3 seconds, and taken out over 10 seconds. The core pin was reversed, and the gel formed on the core pin was dried in an oven at 60° C. for 2 hours to obtain a capsule. The film thicknesses of the obtained capsule in three parts: an upper part (a position 4 mm apart from the top of the column in the height direction), a central part (a position 10 mm apart from the top of the column in the height direction), and a lower part (a position 20 mm apart from the top of the column in the height direction), were measured by using a thickness gauge (manufactured by Mitutoyo Corporation). The measurement was carried out at six positions in each part (positions at intervals of 60 degrees in the circumferential direction), and the averages were calculated. The results are shown in Table 1. The dripping ratio was calculated in accordance with the following equation and the result is shown in Table 1.

Dripping ratio (%)=[(film thickness in center part−film thickness in lower part)/film thickness in center part]×100.

Example 2

The 15 parts by weight of HPMCAS having substitution degrees shown in Table 1 was added to 82.85 parts by weight of water of 15° C., dispersed with a stirrer, and then subjected to addition of 2.15 parts by weight of 10% by weight aqueous ammonia (molar amount equivalent to that of succinyl group) to prepare a test liquid for measurement of thermal gel characteristics of the HPMCAS. The thermal gel characteristics and the capsule moldability were evaluated in the same manner as in Example 1, and the results are shown in Table 1.

Example 3

The 15 parts by weight of HPMCAS having substitution degrees shown in Table 1 was added to 82.55 parts by weight of water of 15° C., dispersed with a stirrer, and then subjected to addition of 2.45 parts by weight of 10% by weight aqueous ammonia (molar amount equivalent to that of the succinyl group) to prepare a test liquid for measurement of thermal gel characteristics of the HPMCAS. The thermal gel characteristics and the capsule moldability were evaluated in the same manner as in Example 1, and the results are shown in Table 1.

Example 4

The 15 parts by weight of HPMCAS having substitution degrees shown in Table 1 was added to 82.36 parts by weight of water of 15° C., dispersed with a stirrer, and then subjected to addition of 2.64 parts by weight of 10% by weight aqueous ammonia (molar amount equivalent to that of the succinyl group) to prepare a test liquid for measurement of thermal gel characteristics of the HPMCAS. The thermal gel characteristics and the capsule moldability were evaluated in the same manner as in Example 1, and the results are shown in Table 1.

Comparative Example 1

The 15 parts by weight of HPMCAS having substitution degrees shown in Table 1 was added to 82.17 parts by weight of water of 15° C., dispersed with a stirrer, and then subjected to addition of 2.83 parts by weight of 10% by weight aqueous ammonia (molar amount equivalent to that of the succinyl group) to prepare a test liquid for measurement of thermal gel characteristics of the HPMCAS. The thermal gel characteristics and the capsule moldability were evaluated in the same manner as in Example 1, and the results are shown in Table 1.

Comparative Example 2

The 15 parts by weight of HPMCAS having substitution degrees shown in Table 1 was added to 81.29 parts by weight of water of 15° C., dispersed with a stirrer, and then subjected to addition of 3.71 parts by weight of 10% by weight aqueous ammonia (molar amount equivalent to that of the succinyl group) to prepare a test liquid for measurement of thermal gel characteristics of the HPMCAS. The thermal gel characteristics and the capsule moldability were evaluated in the same manner as in Example 1, and the results are shown in Table 1.

Comparative Example 3

The 15 parts by weight of HPMCP having substitution degrees shown in Table 1 was added to 79.69 parts by weight of water of 15° C., dispersed with a stirrer, and subjected to addition of 5.31 parts by weight of 10% by weight aqueous ammonia (molar amount equivalent to that of the carboxybenzoyl group) to prepare a test liquid for measurement of thermal gel characteristics of the HPMCP. The thermal gel characteristics and the capsule moldability were evaluated in the same manner as in Example 1, and the results are shown in Table 1.

Example 5

The capsule produced in Example 1 was subjected to the disintegration test in General Test of the Japanese Pharmacopoeia Seventeenth Edition to obtain the disintegration time. As the test liquids, the first liquid (pH: 1.2) and the second liquid (pH: 6.8) were used. Water was also used to further evaluate the water resistance.

Example 6

The capsule produced in Example 2 was subjected to the disintegration test in General Test of the Japanese Pharmacopoeia Seventeenth Edition to obtain the disintegration time. As the test liquids, the first liquid (pH: 1.2) and the second liquid (pH: 6.8) were used. Water was also used to further evaluate the water resistance.

Example 7

The capsule produced in Example 3 was subjected to the disintegration test in General Test of the Japanese Pharmacopoeia Seventeenth Edition to obtain the disintegration time. As the test liquids, the first liquid (pH: 1.2) and the second liquid (pH: 6.8) were used. Water was also used to further evaluate the water resistance.

Example 8

The capsule produced in Example 4 was subjected to the disintegration test in General Test of the Japanese Pharmacopoeia Seventeenth Edition to obtain the disintegration time. As the test liquids, the first liquid (pH: 1.2) and the

TABLE 1

| | substitution degree of each substituent of enteric base material | | | | | | thermal gel characteristics of HPMCAS | | capsule moldability | | | |
| --- | --- | --- | --- | --- | --- | --- | --- | --- | --- | --- | --- | --- |
| | | | | | | | | | | thickness | | |
| | methoxy (DS) | hydroxypropoxy (MS) | acetyl (Ac) (DS) | succinyl (Suc) (DS) | Ac/Suc (—) | carboxybenzoyl (DS) | gelation temp. (° C.) | gel strength G' at 60° C. (Pa) | upper part of capsule (µm) | central part of capsule (µm) | lower part of capsule (µm) | dripping ratio (%) |
| Example 1 | 1.89 | 0.24 | 0.68 | 0.18 | 3.7 | — | 19 | 809 | 125 | 104 | 108 | 3.7 |
| Example 2 | 1.89 | 0.24 | 0.64 | 0.21 | 3.0 | — | 20 | 249 | 121 | 105 | 107 | 1.9 |
| Example 3 | 1.89 | 0.24 | 0.60 | 0.24 | 2.5 | — | 25 | 18.4 | 105 | 110 | 120 | 8.3 |
| Example 4 | 1.88 | 0.17 | 0.61 | 0.26 | 2.3 | — | 26 | 50 | 118 | 115 | 120 | 4.2 |
| Comp. Ex. 1 | 1.88 | 0.24 | 0.54 | 0.28 | 1.9 | — | 80 | 1.52 | 42 | 68 | 86 | 20.9 |
| Comp. EX. 2 | 1.89 | 0.25 | 0.49 | 0.38 | 1.3 | — | >90 | 0.32 | 15 | 30 | 45 | 33.3 |
| Comp. Ex. 3 | 1.90 | 0.25 | — | — | — | 0.61 | >90 | 0.65 | 14 | 32 | 51 | 37.3 |

Each composition for an enteric hard capsule of Examples 1 to 4 gelated thermally around room temperature, and had high gel strength at 60° C., which is assumed to be around the surface temperature of a core pin during molding of an enteric hard capsule. Consequently, the dipping ratio was as small as 10% or less during molding to form a capsule, and the capsule had a uniform film thickness in appearance. On the other hand, each composition for an enteric hard capsule of Comparative Examples 1 to 3 exhibited no thermal gelation characteristics, dripped, and had a high dripping ratio during molding to form a capsule. Hence, a sufficient adhesion amount to a core pin was not obtained, and an enteric hard capsule having sufficient strength was not produced.

second liquid (pH: 6.8) were used. Water was also used to further evaluate the water resistance.

Comparative Example 4

The 10.5 parts by weight of HPMCAS having the same substituents as in Comparative Example 2 was added to 56.9 parts by weight of water of 15° C., dispersed with a stirrer, and then subjected to addition of 2.6 parts by weight of 10% by weight aqueous ammonia (molar amount equivalent to that of the succinyl group), followed by addition of 30 parts by weight of 15% by weight aqueous solution of HPMC having a degree of substitution (DS) with a methoxy group of 1.89 and a molar substitution (MS) with a hydroxypropoxy group of 0.25, to prepare a composition for an enteric hard capsule. Next, the enteric hard capsule was produced in the same manner as in Example 1. The capsule produced was subjected to the disintegration test in General Test of the Japanese Pharmacopoeia Seventeenth Edition to obtain the disintegration time. As the test liquids, the first liquid (pH: 1.2) and the second liquid (pH: 6.8) were used. Water was also used to further evaluate the water resistance.

Comparative Example 5

The 14.3 parts by weight of HPMCP having the same substitution degrees as those in Comparative Example 3 was added to 73.14 parts by weight of water of 15° C., dispersed with a stirrer, and subjected to addition of 5.06 parts by weight of 10% by weight aqueous ammonia (molar amount equivalent to that of the carboxybenzoyl group), followed by addition of 7.5 parts by weight of 10% by weight aqueous agar solution to prepare a composition for an enteric hard capsule. Subsequently, the enteric hard capsule was obtained in the same manner as in Example 1. The capsule produced was subjected to the disintegration test in General Test of the Japanese Pharmacopoeia Seventeenth Edition to obtain the disintegration time. As the test liquids, the first liquid (pH: 1.2) and the second liquid (pH: 6.8) were used. Water was also used to further evaluate the water resistance.

TABLE 2

| | composition for enteric hard capsule (% by weight) | | | | | | disintegration test (minutes) | | |
|---|---|---|---|---|---|---|---|---|---|
| | enteric base material | | neutralizer | | water-soluble gelling agent | | | | |
| | HPMCAS | HPMCP | ammonia | water | HPMC | Agar | Water | pH 1.2 | pH 6.8 |
| Example 5 | 15.0 | — | 0.19 | 84.81 | — | — | 120 or more | 120 or more | 10.1 |
| Example 6 | 15.0 | — | 0.22 | 84.78 | — | — | 120 or more | 120 or more | 8.5 |
| Example 7 | 15.0 | — | 0.25 | 84.75 | — | — | 120 or more | 120 or more | 5.0 |
| Example 8 | 15.0 | — | 0.26 | 82.36 | — | — | 120 or more | 120 or more | 6.2 |
| Comp. Ex. 4 | 10.5 | — | 0.26 | 84.74 | 4.5 | — | 36 | 115 | 3.7 |
| Comp. Ex. 5 | — | 14.3 | 0.53 | 84.47 | — | 0.75 | 3.1 | 105 | 2.5 |

The enteric hard capsules of Examples 5 to 8 had a disintegration time of 120 minutes or more both in water and in the first liquid, which indicated that the enteric hard capsules had excellent water resistance and acid resistance. On the other hand, the composition for an enteric hard capsule containing HPMCAS or HPMCP used in Comparative Example 4 or 5 exhibited no thermal gel characteristics and failed to produce a hard capsule having sufficient strength, so that HPMC or agar as a water-soluble gelling agent was further added. On this account, the capsules had poor water resistance and insufficient acid resistance.

The invention claimed is:

1. A composition for an enteric hard capsule, the composition comprising:
   hypromellose acetate succinate having a molar substitution with a methoxy group per anhydroglucose unit of 1.0 to 2.9, a molar substitution with a hydroxypropoxy group per anhydroglucose unit of 0.1 to 1.0, a molar substitution with an acetyl group per anhydroglucose unit of 0.60 to 0.75 and a ratio of the molar substitution with an acetyl group to a molar substitution with a succinyl group per anhydroglucose unit of 2.0 to 4.0;
   a neutralizer; and
   water, and
   which contains 0% by weight of a gelling agent.

2. The composition for an enteric hard capsule according to claim 1, wherein a 15% by weight aqueous solution of the hypromellose acetate succinate neutralized with ammonia in an amount equivalent to the molar substitution with a succinyl group has a gelation temperature of 5 to 60° C.

3. The composition for an enteric hard capsule according to claim 1, wherein a 15% by weight aqueous solution of the hypromellose acetate succinate neutralized with ammonia in an amount equivalent to the molar substitution with a succinyl group has a gel strength at 60° C. of 10 Pa or more.

4. The composition for an enteric hard capsule according to claim 1, wherein the neutralizer is contained in an amount of 80 to 120% by mole, relative to the molar substitution with a succinyl group in the hypromellose acetate succinate.

5. A method for producing an enteric hard capsule, the method comprising the steps of:
   immersing a core pin heated at 30 to 80° C. in the composition for an enteric hard capsule according to claim 1;
   taking the immersed core pin out of the composition; and
   drying a gel layer of the hypromellose acetate succinate formed on the taken-out core pin.

6. The composition for an enteric hard capsule according to claim 2, wherein a 15% by weight aqueous solution of the hypromellose acetate succinate neutralized with ammonia in an amount equivalent to the molar substitution with a succinyl group has a gel strength at 60° C. of 10 Pa or more.

7. The composition for an enteric hard capsule according to claim 2, wherein the neutralizer is contained in an amount of 80 to 120% by mole, relative to the molar substitution with a succinyl group in the hypromellose acetate succinate.

8. The composition for an enteric hard capsule according to claim 3, wherein the neutralizer is contained in an amount of 80 to 120% by mole, relative to the molar substitution with a succinyl group in the hypromellose acetate succinate.

9. The composition for an enteric hard capsule according to claim 6, wherein the neutralizer is contained in an amount of 80 to 120% by mole, relative to the molar substitution with a succinyl group in the hypromellose acetate succinate.

10. A method for producing an enteric hard capsule, the method comprising the steps of:
    immersing a core pin heated at 30 to 80° C. in the composition for an enteric hard capsule according to claim 2;
    taking the immersed core pin out of the composition; and
    drying a gel layer of the hypromellose acetate succinate formed on the taken-out core pin.

11. A method for producing an enteric hard capsule, the method comprising the steps of:
    immersing a core pin heated at 30 to 80° C. in the composition for an enteric hard capsule according to claim 3;
    taking the immersed core pin out of the composition; and
    drying a gel layer of the hypromellose acetate succinate formed on the taken-out core pin.

12. A method for producing an enteric hard capsule, the method comprising the steps of:
immersing a core pin heated at 30 to 80° C. in the composition for an enteric hard capsule according to claim 4;
taking the immersed core pin out of the composition; and
drying a gel layer of the hypromellose acetate succinate formed on the taken-out core pin.

13. A method for producing an enteric hard capsule, the method comprising the steps of:
immersing a core pin heated at 30 to 80° C. in the composition for an enteric hard capsule according to claim 6;
taking the immersed core pin out of the composition; and
drying a gel layer of the hypromellose acetate succinate formed on the taken-out core pin.

14. A method for producing an enteric hard capsule, the method comprising the steps of:
immersing a core pin heated at 30 to 80° C. in the composition for an enteric hard capsule according to claim 7;
taking the immersed core pin out of the composition; and
drying a gel layer of the hypromellose acetate succinate formed on the taken-out core pin.

15. A method for producing an enteric hard capsule, the method comprising the steps of:
immersing a core pin heated at 30 to 80° C. in the composition for an enteric hard capsule according to claim 8;
taking the immersed core pin out of the composition; and
drying a gel layer of the hypromellose acetate succinate formed on the taken-out core pin.

16. A method for producing an enteric hard capsule, the method comprising the steps of:
immersing a core pin heated at 30 to 80° C. in the composition for an enteric hard capsule according to claim 9;
taking the immersed core pin out of the composition; and
drying a gel layer of the hypromellose acetate succinate formed on the taken-out core pin.

17. The composition for an enteric hard capsule according to claim 1, wherein the hypromellose acetate succinate has a ratio of the molar substitution with an acetyl group to a molar substitution with a succinyl group per anhydroglucose unit of 2.3 to 4.0.

18. The composition for an enteric hard capsule according to claim 1, wherein the hypromellose acetate succinate has a molar substitution with an acetyl group per anhydroglucose unit of 0.60 to 0.70 and a ratio of the molar substitution with an acetyl group to a molar substitution with a succinyl group per anhydroglucose unit of 2.5 to 3.7.

19. The composition for an enteric hard capsule according to claim 1, wherein the hypromellose acetate succinate has a molar substitution with a methoxy group per anhydroglucose unit of 1.7 to 2.0, and a molar substitution with a hydroxypropoxy group per anhydroglucose unit of 0.15 to 0.28.

20. The composition for an enteric hard capsule according to claim 1, wherein the water is present in an amount of 70 to 90% by weight of the composition.

* * * * *